United States Patent
Renesto et al.

(10) Patent No.: US 8,862,230 B2
(45) Date of Patent: Oct. 14, 2014

(54) PACING CONFIGURATION FOR AN IMPLANTABLE MEDICAL DEVICE

(71) Applicant: Sorin CRM SAS, Clamart (FR)

(72) Inventors: Fabrizio Renesto, Borgofranco d'Ivrea (IT); Lionel Giorgis, Saint Brieuc (FR)

(73) Assignee: Sorin CRM S.A.S., Clamart Cedex (FR)

( * ) Notice: Subject to any disclaimer, the term of this patent is extended or adjusted under 35 U.S.C. 154(b) by 0 days.

(21) Appl. No.: 14/263,643

(22) Filed: Apr. 28, 2014

(65) Prior Publication Data

US 2014/0236251 A1    Aug. 21, 2014

Related U.S. Application Data

(63) Continuation of application No. 13/411,412, filed on Mar. 2, 2012, now Pat. No. 8,712,526.

(30) Foreign Application Priority Data

Mar. 3, 2011    (FR) ...................................... 11 51729

(51) Int. Cl.
*A61N 1/00*    (2006.01)
*A61N 1/365*    (2006.01)

(52) U.S. Cl.
CPC .................................. *A61N 1/36578* (2013.01)
USPC .................................... 607/17; 607/9; 607/28

(58) Field of Classification Search
CPC A61N 1/365; A61N 1/36514; A61N 1/36578
See application file for complete search history.

(56) References Cited

U.S. PATENT DOCUMENTS

| | | | |
|---|---|---|---|
| 5,304,208 A | 4/1994 | Inguaggiato et al. | |
| 6,556,866 B2 | 4/2003 | Dal Molin et al. | |
| 7,664,547 B2 | 2/2010 | Plicchi et al. | |
| 2008/0177343 A1 | 7/2008 | Dal Molin et al. | |
| 2009/0192572 A1 | 7/2009 | Dal Molin et al. | |
| 2009/0209875 A1 | 8/2009 | Giorgis et al. | |

FOREIGN PATENT DOCUMENTS

| | | |
|---|---|---|
| EP | 0515319 | 11/1992 |
| EP | 1108446 | 6/2001 |
| EP | 1736203 | 12/2006 |
| EP | 1938861 | 7/2008 |
| EP | 2082684 | 7/2009 |
| EP | 2092885 | 8/2009 |
| WO | WO 2006/049538 | 5/2006 |

OTHER PUBLICATIONS

Foreign Search Report received for French Appln. No. 1151729 dated Jul. 14, 2011.

Notice of Allowance received for U.S. Appl. No. 13/411,412 dated Dec. 2, 2013.

*Primary Examiner* — Christopher D Koharski
*Assistant Examiner* — Philip Edwards
(74) *Attorney, Agent, or Firm* — Foley & Lardner LLP (57) ABSTRACT

An implantable medical device includes a sensor configured to generate an endocardial acceleration (EA) signal representative of activity of a patient's heart. The device further includes one or more circuits configured to identify within the EA signal at least one EA signal component corresponding to at least one peak of endocardial acceleration, and extract from the at least one EA signal component at least two characteristic parameters. The one or more circuits are further configured to generate a composite index based on a combination of the at least two characteristic parameters, determine a plurality of values of the composite index for a plurality of pacing configurations, and select a current pacing configuration from among the plurality of pacing configurations based on the plurality of values of the composite index.

25 Claims, 4 Drawing Sheets

PACING CONFIGURATION FOR AN IMPLANTABLE MEDICAL DEVICE

CROSS REFERENCE TO RELATED APPLICATIONS

This application is a continuation of U.S. patent application Ser. No. 13/411,412, filed Mar. 2, 2012, which claims the benefit of and priority to French Patent Application No. 1151729, filed Mar. 3, 2011, both of which are hereby incorporated by reference herein in their entireties.

BACKGROUND

The present invention relates to "active implantable medical devices" as defined by the 20 Jun. 1990 Directive 90/385/EEC of the Council of the European Communities, and more particularly to those devices that continuously monitor a patient's heart rhythm and deliver to the heart, if necessary, electrical pulses for joint and permanent stimulation of the left and the right ventricles, so as to resynchronize them, said technique being known as Cardiac Resynchronization Therapy ("CRT") or Bi-Ventricular Pacing ("BVP").

Cardiac resynchronization is known whereby a patient is implanted with a device equipped with electrodes to stimulate various sites in both ventricles (often called a CRT device or CRT pacemaker). The CRT device typically applies between the respective moments of stimulation of the left and right ventricles a delay that is called an "interventricular delay" (VVD) which VVD is adjusted to resynchronize the contraction of both ventricles to optimize the patient's hemodynamic status.

A CRT pacemaker is for example disclosed in EP 1108446 A1 and its counterpart U.S. Pat. No. 6,556,866 (both assigned to Sorin CRM S.A.S., previously known as ELA Medical), which describes a CRT device for applying between the two ventricular pacing sites a variable VVD, adjusted to resynchronize the contractions of the ventricles with a fine optimization of the patient's hemodynamic status. The VVD may be zero (meaning that the left and right ventricles are stimulated essentially simultaneously), positive (meaning that the left ventricle is stimulated after the right ventricle) or negative (meaning that the right ventricle is stimulated after the left ventricle).

Clinical studies have often observed a dramatic improvement in results for patients diagnosed with heart failure that is not improved by conventional therapy, because the parameters of the CRT therapy have been precisely adjusted according to the patient and to the nature of the patient's disorder.

But the implementation of CRT devices remains a very delicate intervention for the practitioner, because of the many choices that must be made. First, it must be determined for each of the leads the best stimulation site. The physical locations of the pacing electrodes for each lead relative to the myocardial tissue are called "pacing sites"; generally, these pacing sites can only be selected at implantation, by appropriate positioning of the electrodes. It is important to verify the effectiveness of the selected pacing sites, due to the possible influence of long-term efficacy of the resynchronization therapy. In some cases, the CRT device has several multi-site electrodes placed in the same cavity, and a change of pacing site(s) for delivering stimulation pulses in this cavity is possible by internal switching of the device.

In any case, during the intervention, the practitioner tests several possible pacing sites by successive repositioning of the lead to find the one that he believes is the most appropriate.

Another aspect of the development of these CRT devices is the increasing number of electrodes, especially for "multi-site" devices that allow selecting the pacing sites used for the delivery of stimulation pulses and detection of myocardial potentials (e.g., from spontaneous cardiac events) and optimizing the operation of the CRT device.

The increasing number of electrodes can also result from the presence at the same level of the lead of several sectorial electrodes (electrodes specifically directed in a radial direction relative to the lead, at the pacing site), with the possibility to select one or the other of these sectorial electrodes to optimize the delivery of pulses to the selected pacing site. This is particularly true for leads implanted in the coronary venous system, for indirect stimulation of a left cavity: with several sectorial electrodes, it is possible to select one that is turned towards the epicardium wall facing the cavity in contact with this wall.

Second, with the development of implantable medical devices for stimulation of more than two ventricular sites, it is necessary to determine whether this *** "tri-ventricular" or "multi-ventricular" mode of stimulation is or is not preferable to a conventional "bi-ventricular" pacing mode.

Thus, the practitioner may be faced with a choice between a standard mode of bi-ventricular pacing (right and left ventricles), a tri-ventricular pacing mode (simultaneous stimulation by three electrodes, with an additional electrode in the right or left cavity), or even multi-ventricular (with multi-electrode leads for which multiple electrodes of the same lead are used concurrently). By appropriate switching, the practitioner can choose the most appropriate stimulation mode, but the number of possible configurations increases very rapidly with the increase of the electrodes, making the task all the more difficult for the practitioner, faced with a choice between a large number of different configurations.

Third, the device should be set properly, including the atrioventricular delay (AVD) and interventricular delay (VVD).

The many opportunities arising from these various choices are referred to as "pacing configurations."

Indeed, it appears that today, even with full implementation of procedures, there are approximately 30% of patients who do not respond to CRT therapy, with serious consequences that can be imagined in terms of quality of life, hospitalizations for heart failure and reduced life expectancy.

Most studies now focus on methods to treat this refractory patient population by testing new stimulation configurations, and seeking to optimize the stimulation setting, during the implantation as well as on an ongoing basis, by periodic reassessments.

There is thus a real need for a technique to evaluate, according to a simple, rapid, automated and precise method, the impact of the choice of the stimulation sites and of the parameters of CRT therapy, especially the AVD and VVD, so as to optimize the patient's hemodynamic status.

The reference technique for the adjustment of CRT stimulation parameters is an assessment by echocardiography with estimation of the characteristic delays of the systole, in particular the delay of opening of the aortic valve. This procedure, which must be implemented in hospitals and by qualified personnel, is time consuming and expensive and cannot be applied as often as would be useful or necessary. In addition, it is not easy to perform ultrasound measurements during the implantation procedure, as the sterile field does not allow easy access to the patient's chest with the ultrasound probe.

Other techniques have been proposed to evaluate the effectiveness of the choice of stimulation pacing sites and of the setting of CRT therapy parameters. Thus, EP 1736203 A1 and its US counterpart U.S. Pat. No. 7,664,547 (both assigned to Sorin CRM S.A.S, previously known as ELA Medical) describe a CRT device that uses for this purpose the parameters related to endocardial acceleration (hereinafter "EA") to determine an optimal pacing configuration, at the time of implantation or thereafter.

Indeed, it may be necessary to reassess these choices later, after the initial implantation, and eventually readjust the settings. The benefits provided by CRT therapy can ultimately lead to change the initial configuration and setup of the stimulation.

Indeed, several clinical studies have shown that endocardial acceleration is a parameter that accurately and in real-time reflects phenomena related to the movements of the heart chamber, and can therefore provide comprehensive information on the mechanical heart, both in the case of normal operation and in the case of a deficient operation. Endocardial acceleration is for example measured by an accelerometer integrated into an endocardial lead, as described for example in EP 0515319 A1 and its US counterpart U.S. Pat. No. 5,304,208 (both assigned to Sorin Biomedica Cardio SpA).

WO 2006/049538 A1 (St. Jude Medical AB) describes a known technique to evaluate a physiological parameter that reflects the hemodynamic performance of the heart for a given stimulation configuration, from various sensors (pressure, acceleration, acoustic) placed on one or more leads, some of them being possibly repositioned; thus the signal delivered by these sensors depends on the current position of the lead and cannot be a reliable reference. However, the proposed technique has a number of drawbacks, including the fact that the optimization is based on the analysis of a single physiological parameter (e.g., cardiac output, stroke volume). However, some patients may be more or less sensitive to either of these parameters, which is not always the same from one patient to another because of the specific response of the patient, his pathology and the evolution of it. Further, the analyzed parameter is not necessarily the most relevant relatively to the changes in the stimulation configuration.

SUMMARY

It is, therefore, an object of the present invention to propose a system or apparatus that can help the practitioner find the pacing configuration that is the most appropriate, especially to enable the practitioner to evaluate the effectiveness of modifications to pacing configurations due to repositioning of the lead and, where appropriate, selections of additional leads (bi-ventricular, tri-ventricular or multiventricular pacing) or switching of electrodes in the case of a multi-electrode lead.

It is another object of the present invention to provide a technique for evaluating the pacing configuration with an increased sensitivity and specificity compared to what has been proposed to date, including the EP 1736203 A1 cited above, particularly with respect to changes of position of the pacing electrodes.

It is another object of the present invention to define indexes of cardiac hemodynamic performance of the patient, to optimize the positioning of the leads and the choice of configurations of the CRT pacemaker during the implantation procedure, and the possible reprogramming of any parameter after the CRT device implantation.

Another object of the present invention is to provide complete equipment, made available to the implanting practitioner, which is specifically adapted to the selection of stimulation pacing sites during the process of implantation of the leads and of a bi-ventricular, tri-ventricular or multi-ventricular device.

To this end, the present invention is broadly directed to a system for seeking an optimal pacing configuration for an active medical device (implantable cardiac prosthesis or external device used temporarily) implementing CRT by bi-, tri- or multiventricular pacing, this system including, as taught by and disclosed in EP 1736203 A1 cited above, to which one skilled in the art is referred:

means for ventricular pacing, able to deliver stimulation pacing pulses to be applied to electrodes located respectively at least at one right ventricular pacing site and at least at one left ventricular pacing site according to a predetermined pacing configuration that is current and modifiable;

an acceleration sensor for delivering an endocardial acceleration (EA) signal representative of cyclical contractions and relaxations of the heart, and means for isolating and preprocessing in the EA signal during a given cardiac cycle between two successive ventricular events: (i) an EA1 component corresponding to the first peak of endocardial acceleration associated with the isovolumetric ventricular contraction, and (ii) an EA2 component corresponding to the second peak of endocardial acceleration associated with the isovolumetric ventricular relaxation.

It is another aspect of the present invention to assess the efficiency of stimulation based on a "performance index" compiled from parameters from a signal delivered by an endocardial acceleration sensor, including: the amplitude of the first endocardial acceleration peak, the duration of this peak, and the duration of systole (i.e., the interval between the first and second peaks of endocardial acceleration).

Preferably, a system in accordance with the present invention further includes means for evaluating the effectiveness of the current pacing configuration, including:

means for extracting at least two parameters from the isolated and preprocessed EA1 and EA2 components:
means for combining said at least two parameters in a composite index representative of the effectiveness of that current pacing configuration;
means for determining a plurality of values of said composite index for a corresponding plurality of different pacing configurations, and
means for determining a preferred pacing configuration from said plurality of values of said composite index by searching for an optimum of that composite index.

In a preferred embodiment, said at least two parameters characteristic of the EA1 and EA2 components are parameters selected from among the group consisting of:

PEA1=value of the peak-to-peak EA1 component;

TstEA1=duration of occurrence of the beginning of the EA1 component represented by the time interval between i) a temporal marker of the beginning of the cardiac cycle and ii) the crossing of an energy envelope threshold of the EA1 component;

LargEA1=time interval between i) said crossing of the energy envelope threshold, and ii) the instant of the peak of said energy envelope of the EA1 component; and Syst=duration of systole, represented by the time interval between the beginning of the EA1 component and the beginning of the EA2 component.

In one embodiment, the composite index is an index selected from among the group consisting of:

$$Ind1 = (TstEA1 \times LargEA1)/(Syst \times PEA1);$$

$$Ind2 = (TstEA1 \times LargEA1)/[(Syst - LargEA1) \times PEA1];$$

$$Ind3=(TstEA1 \times LargEA1)/(Syst); \text{ and/or}$$

$$Ind4=(TstEA1)/(PEA1),$$

said optimum being a minimum of the indexes.

The system advantageously comprises an atrial lead carrying the endocardial acceleration sensor, and left and right ventricular leads with their distal electrode respectively defining the pacing site(s) for right and left ventricular pacing according to the current pacing configuration. It may also include an additional, right or left, ventricular lead carrying at its distal end electrodes for definition of at least one additional pacing site for ventricular pacing, defining the current pacing configuration in combination with the right and left ventricular pacing site(s).

Another embodiment of the present invention is directed to a system including:

An implantable active medical device capable of delivering CRT by bi-, tri- or multi-ventricular stimulation;

An atrial lead carrying an endocardial acceleration sensor;

Right and left ventricular leads respectively carrying distal electrodes for definition of the right and left ventricular pacing sites according to a current pacing configuration;

Optionally an additional, right or left, ventricular lead carrying at its distal end electrodes for definition of at least one additional ventricular pacing site, defining the current pacing configuration in combination with the right and left ventricular pacing site(s);

An external device for providing cardiac detection/stimulation for a patient;

An interface unit comprising means for processing an EA signal, provided by said EA sensor, and means for coupling the external equipment to the atrial and ventricular leads; and External programmer means, coupled to the interface housing for reception of the processed EA signal, including the means for evaluating the effectiveness of the pacing configuration.

One embodiment relates to a memory device having instructions stored thereon that, when executed by a processor of an implantable medical device, cause the implantable medical device to perform operations. The operations include generating, using an acceleration sensor of the implantable medical device, an endocardial acceleration (EA) signal representative of activity of a patient's heart. The operations further include identifying within the EA signal a first EA signal component corresponding to a first peak of endocardial acceleration and a second EA signal component corresponding to a second peak of endocardial acceleration. The operations also include extracting from at least one of the first EA signal component and the second EA signal component at least two characteristic parameters, the at least two characteristic parameters relating to at least two different types of characteristics of the at least one of the first EA signal component and the second EA signal component. The at least two different types of characteristics to which the at least two characteristic parameters relate are selected from among the following:

a peak-to-peak amplitude (PEA1) of the first EA signal component;

a first time interval (TstEA1) between a beginning of a cardiac cycle and a beginning of the first EA signal component;

a second time interval (LargEA1) between the beginning of the first EA signal component and a peak associated with the first EA signal component; or a third time interval (Syst) representative of a duration of a systole, the third time interval between the beginning of the first EA signal component and a beginning of the second EA signal component.

The operations may further include generating a composite index based on a combination of the at least two characteristic parameters, wherein the composite index is selected from among the following:

$$Ind1=(TstEA1 \times LargEA1)/(Syst \times PEA1);$$

$$Ind2=(TstEA1 \times LargEA1)/[(Syst-LargEA1) \times PEA1];$$

$$Ind3=(TstEA1 \times LargEA1)/(Syst); \text{ or}$$

$$Ind4=(TstEA1)/(PEA1);$$

The operations may further include determining a plurality of values of the composite index for a plurality of pacing configurations. The operations may further include selecting a current pacing configuration for the implantable medical device from among the plurality of pacing configurations based on the plurality of values of the composite index.

DETAILED DESCRIPTION

With reference to the drawing FIGS. 1-6, a preferred embodiment of an apparatus according to the present invention will now be described.

The present invention may particularly be applied to active implantable medical devices such as those of the Paradym CRT device family produced and marketed by Sorin CRM, Clamart France, formerly known as ELA Medical, Montrouge, France. These devices include programmable microprocessor circuitry to receive, format, and process electrical signals collected (detected) by electrodes implanted in a patient, and deliver stimulation pulses to these electrodes. It is possible to transmit by telemetry software that will be stored in a memory of the implantable devices and executed to implement the functions of the invention that will be described herein. The adaptation of these devices to implement the functions and features of the present invention is believed to be within the abilities of a person of ordinary skill in the art, and therefore will not be described in detail.

The technique of the present invention is based on the analysis of endocardial acceleration (hereinafter "EA"), which is a parameter that accurately and in real time reflects the phenomena contributing to the mechanical operation of the myocardium and may be measured by an accelerometer coupled to the heart muscle, as described for example in EP 0515319 A1 (and its counterpart: U.S. Pat. No. 5,304,208) (Sorin Biomedica Cardio SpA). This document teaches a method to collect an EA signal through an endocardial lead equipped with a distal stimulation electrode implanted in the atrium or ventricle and integrating a microaccelerometer to measure endocardial acceleration.

Note however that, although in the present description it is referred mainly to the analysis of an EA signal delivered by a sensor placed on an endocardial lead, the invention is also applicable to an analysis conducted from an EA signal delivered by other types of implanted sensors, such as a myocardium wall motion sensor, an epicardial sensor or an accelerometer placed in the case of an implant. The invention is also applicable to the analysis of a noninvasively collected external EA signal, e.g., from a sensor attached to the patient's chest at the sternum.

Figure 1:
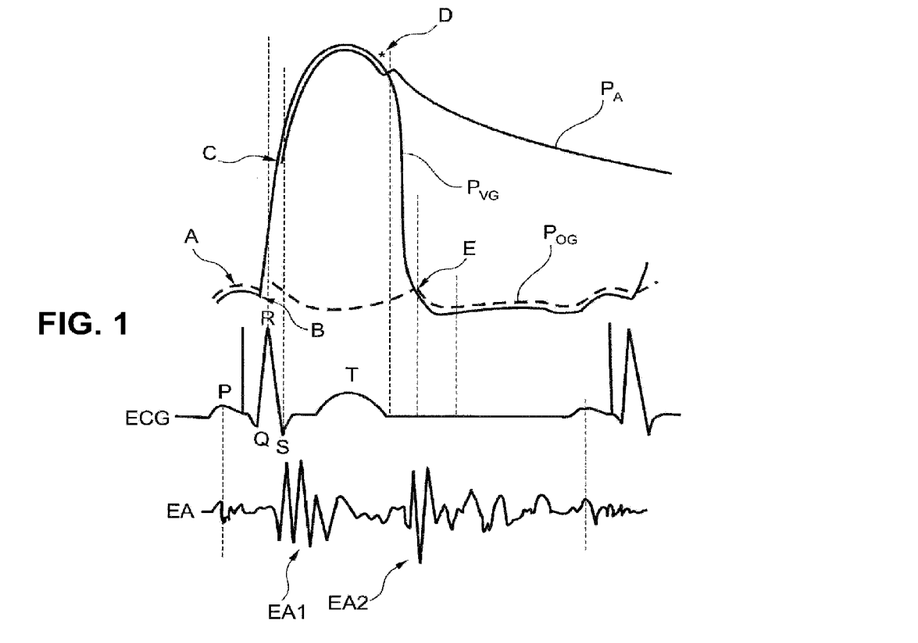
FIG. 1 is a series of three timing diagrams illustrating various signals characterizing the cardiac activity during a given cycle.

FIG. 1 shows the different signals characterizing the activity of a patient's heart during a cardiac cycle, with: the profile of intracardiac pressures ($P_A$, $P_{VG}$ and $P_{OG}$), a record of surface electrocardiogram (ECG), and the variations of the endocardiac acceleration (EA) signal. The characteristic $P_A$ shows the variations in the aortic pressure, $P_{VG}$ in the left ventricular pressure and $P_{OG}$ in the left atrium pressure. Points A to E correspond to the different following phases: A contraction of the left atrium, B closure of the mitral valve, C opening of the aortic valve, D closure of the aortic valve, E opening of the mitral valve. The ECG signal has successively the P wave corresponding to the depolarization of the atria, the QRS complex corresponding to the depolarization of the ventricles, and the T wave corresponding to the ventricular repolarization.

The EA signal collected during a given cardiac cycle forms two main components, corresponding to the two major heart sounds (S1 and S2 sounds of phonocardiogram) that can be recognized in each cardiac cycle:

the EA1 component, starting after the QRS complex is caused by a combination of the closure of the atrioventricular valves, the opening of the semilunar valves and the contraction of the left ventricle. The amplitude variations of this EA1 component are closely related to the changes in pressure in the ventricle (the maximum peak to peak amplitude being specifically correlated with the positive maximum of dP/dt pressure variation in the left ventricle) and thus can provide a parameter representative of the myocardium contractility, which is itself linked to the level of activity of the sympathetic system; and the EA2 component occurs during the phase of isovolumetric ventricular relaxation. It accompanies the end of ventricular systole and is mainly produced by the closure of the aortic and pulmonary valves.

For one implementation of the present invention, it is first necessary to extract from the EA signal, the endocardial acceleration and more specifically the two components EA1 and EA2, characteristics correlated with time intervals of the systole and to other myocardium hemodynamic performance indexes, by specific processing of this EA signal.

The preliminary processing of the EA components preferably involves, first, to individualize the successive cardiac cycles in the EA signal that is continuously collected, identifying markers of the beginning of the cycle to separate these cycles and isolate a series of EA sub-signals bounded in time, each corresponding to a period of one cardiac cycle.

In the case of an endocardial EA signal, the time markers of the beginning of the cycle may be provided by the implant itself or by an external device during implantation, which according to the mode stores the timings of V pacing, or the timings of R-wave detection. The temporal marker of the beginning of the cycle, which is the origin of time, is designated "0".

The next step is to isolate the EA1 and EA2 components in each sub-signal bounded in time corresponding to one cardiac cycle. Each of these EA1 and EA2 components are represented by a set of successive values describing the continuous variation of the EA signal in a given time window extending around the peak of the EA signal (PEA1 peak or PEA2 peak), for a fraction of the duration of a cardiac cycle. Specifically, each component consists of a subset of the EA signal samples obtained after digitization of this signal over the duration of the cardiac cycle.

Each of these components represents a fraction of the EA signal on the duration of a cardiac cycle, each cardiac cycle comprising a plurality of different components that occur in succession, including the first two components EA1 and EA2, which are followed by secondary components known in the art as EA3 and EA4.

Preferably, the EA1 and EA2 components of the signal EA are determined with an averaging over several cycles, typically three to five cycles, using a technique such as that described in EP 2092885 A1 (and its counterpart: US Patent Publication No. 2009/0209875) (both assigned to Sorin CRM S.A.S., previously known as ELA Medical), a technique that allows including the elimination of the cycle to cycle variations by a time readjustment of the successive components before averaging.

Essentially, this technique is to perform a preprocessing of the EA signal continuously collected, with:

Division of the EA signal into sub-signals each corresponding to the duration of one cardiac cycle and identified by a marker of cycle beginning to achieve this division;

Segmentation of each of these sub-signals in order to individualize the EA1 and EA2 components in a given temporal window;

For the current EA1 or EA2 component thus isolated on a cycle, seeking for a cross-correlation peak with respect to the EA1 (or EA2) components from the other collected cycles;

Calculation of a corresponding temporal shift; and

Application of the temporal shift thus calculated to the current component, so as to align it with the others.

The analysis processing can then be performed on these successive EA1 and EA2 components, with elimination of the bias of the cycle to cycle variability as a result of the preprocessing.

In one embodiment, the present invention is based on the extraction and analysis of a number of characteristic parameters of the EA1 and EA2 components, parameters which are then combined to give composite indexes that the practitioner seeks to optimize (minimize or maximize depending on the cases), the reached optimum reflecting the best pacing configuration among all those that have been tested.

Figure 2:
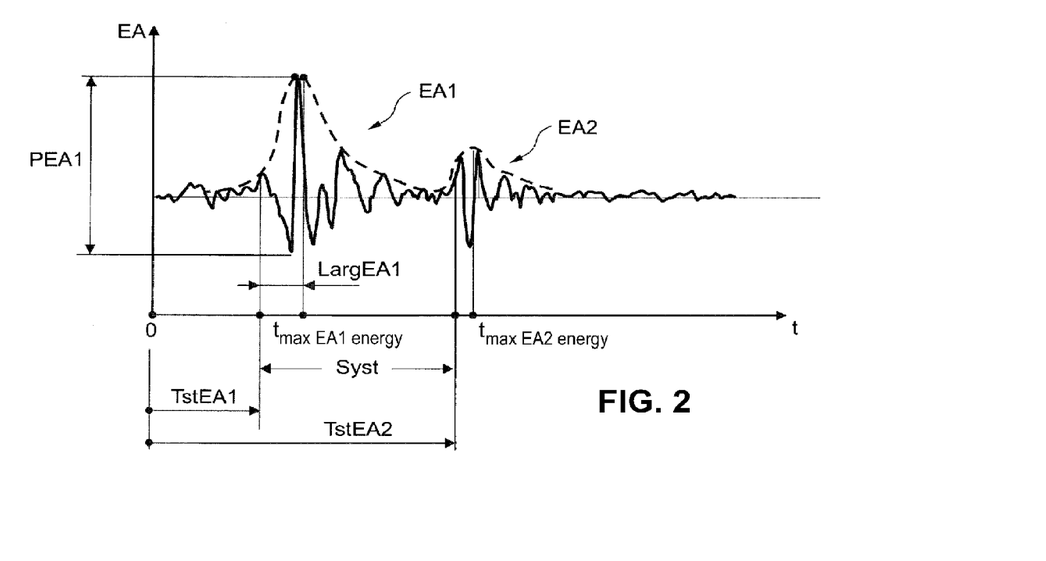
FIG. 2 illustrates, in more detail, the shape of the endocardial acceleration signal during a given cardiac cycle, with the various parameters used for the implementation of the invention.

These parameters are four in number, and are illustrated in FIG. 2 which shows the variation of the EA signal during one cardiac cycle, with its two EA1 and EA2 components.

The peak-to-peak component EA1, designated PEA1;

The timing of the beginning of the EA1 component, denoted TstEA1, which is a period counted from the time origin O in FIG. 2;

An indicator of the duration of the EA1 component, designated LargEA1, which is the time interval between the instant TstEA1 from the instant $t_{maxEA1energy}$ of the energy peak of the EA1 component; and The duration of systole, designated Syst, corresponding to the time interval between TstEA1, which marks the beginning of the EA1 component, and TstEA2, which marks the beginning of the EA2 component.

The timings TstEA1 and TstEA2 of start of the EA1 and EA2 components can be obtained by thresholding an envelope of energy obtained by squaring the value of the signal samples (envelope shown in dashed lines in FIG. 2), then applying a smoothing window of 100 ms, for example. The timings TstEA1 and TstEA2 correspond to a threshold that can be for example 10% of the maximum energy of the considered window corresponding to the one and the other of two EA1 and EA2 components.

The respective timings of occurrence of the maximum energy of the EA1 and EA2 components, denoted $t_{maxEA1energy}$ and $t_{maxEA2energy}$, are used to calculate in particular the LargEA1=$t_{maxEA1energy}$−TstEA1.

This method for determining characteristic instants of the EA1 and EA2 components is described as well as others in EP 2092885 A1 and its counterpart US Patent Publication No. 2009/0209875 cited above, which can be referred for more details and are incorporated herein by reference in their entirety.

The above parameters are chosen for the following reasons:

the PEA1 amplitude is associated with the cardiac contractility (clinical studies have shown a strong correlation with the maximum LVdP/dT). Effective stimulation for an optimal position of the pacing electrode, has the effect of maximizing this parameter.

The timing of occurrence of the beginning of the EA1 component TstEA1 is associated with the phase of isovolumetric contraction of the cardiac cycle, particularly at the instant of opening of the aortic valve, timing also known as "Left Pre-Ejection Interval", LPEI. Clinical studies suggest that minimization of this parameter reflects an improvement in ventricular resynchronization and hemodynamic performance. It can also be found that this parameter is also very sensitive to changes in position of the electrodes of the lead.

The duration LargEA1 is a good indicator of the resynchronization. Reduced values should be sought for the duration of this value. It was also found that this parameter is much more sensitive to changes in the positions of the electrodes, in particular, the full length of the EA1 component (time interval between the beginning and the end of the EA1 component). It is also more reliable than a technique of using the instant of the end of the EA component by detecting it by thresholding and averaging over several cycles: a relatively high variability is then found compared to the moment the peak is reached.

The duration of systole Syst is associated with the time between the closure of the mitral valve and that of the aortic valve. This parameter gives a good indication of the performance of the ejection phase. This parameter is also very sensitive to changes in position of the electrodes.

In other words, the above four parameters have a particularly high sensitivity and accuracy in response to changes in pacing configurations, which very effectively guides the practitioner in the selection and adjustment of the pacing sites.

These parameters are also sensitive to the pacemaker settings (including AVD and VVD delays), and may be used for initial adjustment or later readjustment.

However, the optimization of one of the four above parameters is not always sufficient to determine with certainty the best pacing configuration and the best settings of the device. The use of a single parameter in fact leads to an excessive number of incorrect determinations, which is why the present invention proposes to combine a plurality of these parameters (at least two) in one or more indexes called "composite indexes" to reliably determine the best choice of pacing configuration.

The following composite indexes were chosen because they are all very sensitive to changes in position of the pacing sites:

Ind1=(TstEA1×LargEA1)/(Syst×PEA1): This index combines the various characteristic durations of the cardiac cycle and the parameters reflecting contractility, and has the highest sensitivity to changes in the position of the pacing sites and the best correlation with the clinical references;

Ind2=(TstEA1×LargEA1)/[(Syst−LargEA1)×PEA1]: This index is very similar to the previous one, but the difference Syst−LargEA1 enables more stability in the factor related to the duration of systole;

Ind3=(TstEA1×LargEA1)/(Syst): This index is derived from the first one, without contribution of contractility and is more suitable for applications in which optimization is strictly related to the timings of the cardiac cycle and is not or is little dependent of contractility;

Ind4=(TstEA1)/(PEA1): This index is a subsidiary index and reflects cardiac performance when optimization is only those of the phase of ventricular contraction. It can particularly be used if the closure of the aortic valve is difficult to detect (that is, when the EA2 component is hardly visible), leading to an uncertain determination of the duration of systole Syst, because of an unreliable signal related to the relaxation phase of the cardiac cycle.

For all these indexes, the optimum to seek is the minimum.

The composite indexes above have proved to be very effective in clinical studies, and adapted to many different hemodynamic conditions of patients, for various pathologies.

This list is not exhaustive, and persons having ordinary skill in the art would understand that other combinations of the parameters listed above can be used in other situations or particular pathologies.

A preferred method to achieve, in practice, an optimization in accordance with the present invention during the implantation phase, with reference to FIGS. 3-5, will now be described.

Figure 3:
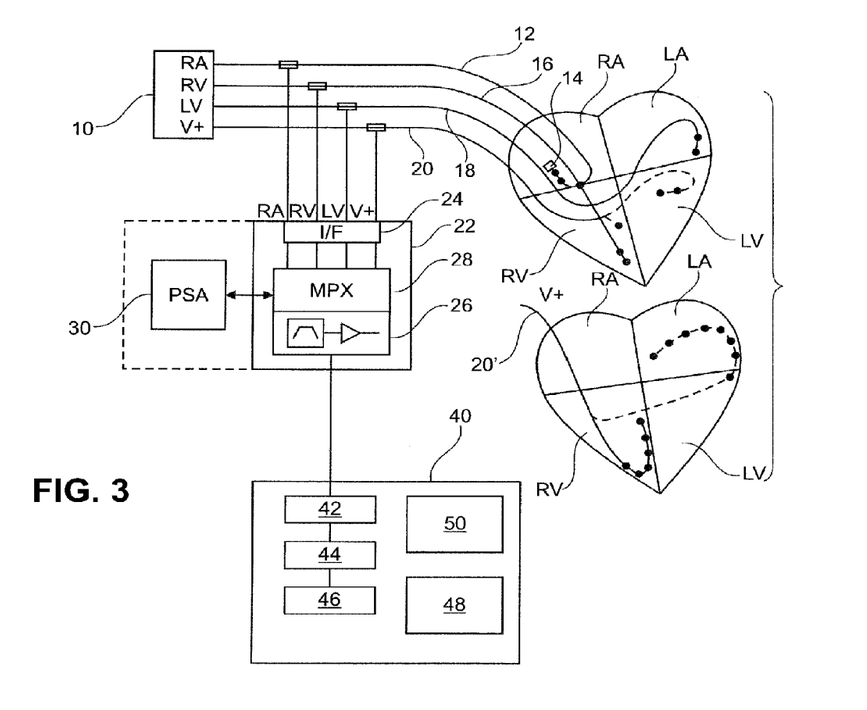
FIG. 3 schematically illustrates the various elements of a preferred embodiment of the present invention in the form of functional block diagrams, of the equipment available to the practitioner at the time of implantation for the selection of the pacing sites of the invention.
Figure 4:
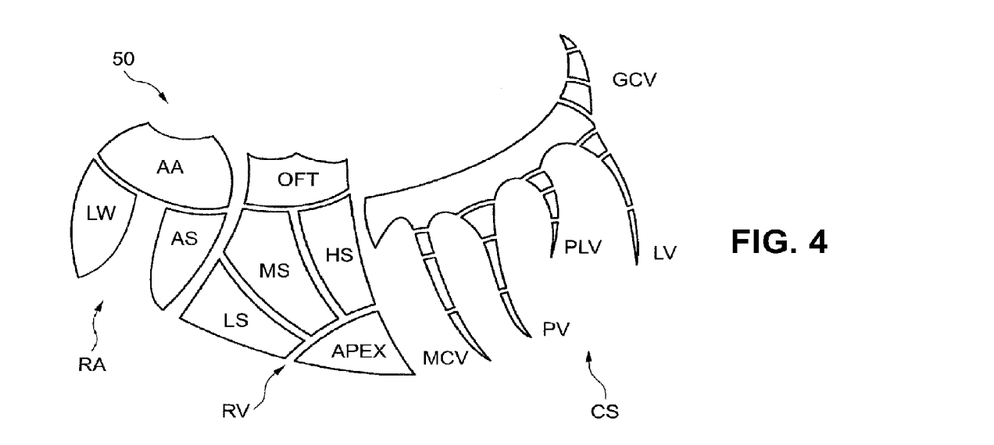
FIG. 4 illustrates a diagram displayed by the interface of FIG. 3 for selection of the pacing sites.

FIG. 3 schematically shows the facility used to optimize the position of the pacing sites and of the programmed parameter configurations. The system includes a CRT pacemaker and/or resynchronizer implantable medical device 10, provided with a plurality of leads implanted in the heart with a right atrial lead RA, referenced 12, equipped at its distal end with an EA sensor, e.g., an accelerometer for delivering an EA signal 14. Note that the EA sensor is placed on an atrial lead, which is therefore another lead than those to be displaced to find an optimal pacing configuration. In other words, the lead on which the EA sensor is placed is not involved in the definition of the "pacing configuration" in the sense described above.

The device is also connected to right ventricular RV and left ventricular LV leads, referenced 16, 18, and possibly to an additional ventricular lead V+, referenced 20, which can be used to improve the ventricular performances, especially if pacing by the RV and LV lead does not provide sufficient improvement in hemodynamics.

These leads are directly connected to the generator 10 and temporarily, via sterile cables, to an interface unit 22 for seeking of the optimal pacing configuration.

The ventricular lead may also be, as shown in 20' on the variation in the lower right heart scheme, a ventricular right or left "multi-electrode" lead. The EP 1938861 A1 (and counterpart: U.S. Patent Publication No. 2008/0177343) and EP 2082684 A1 (and counterpart: US Patent Publication No.

2009/0192572) (both on behalf of Sorin CRM S.A.S., previously known as ELA Medical) describe such a lead having a plurality of electrodes near its distal end, for example, ten electrodes, associated with a chip, hermetically encapsulated in the vicinity of the electrodes in a rigid ring, providing the multiplexing/demultiplexing of the electrodes with a common bus having two insulated conductors extending along the entire length of the lead to the proximal connector for coupling with the generator, the latter being equipped with a counterpart circuit for demultiplexing/multiplexing.

The interface housing 22 includes a proper interface 24 for receiving signals from the electrodes RA, RV, LV and V+, or delivery of pacing pulses on these same conductors. A stage 26 is used to filter and amplify the various detected depolarization signals and the EA signal. A multiplexer 28 also selectively ensures switching of the various conductors with a Pacemaker System Analyzer ("PSA") or temporary pacing system 30 for external stimulation, possibly included in the interface unit 22, designed to continuously ensure functions of detection and generation of stimulation pulses during testing of the different configurations, in relay of the implanted generator 10 or before connecting it to the leads 12, 16, 18 and 20.

The system also includes a programmer 40 or another computer system, comprising a software module for the acquisition and processing of EA and cardiac depolarization signals, particularly for calculating one or more of the composite indexes Ind1 to Ind4, in accordance with the present invention. This programmer 40 includes a processing unit 42, a measurement unit 44 and a storage memory 46. It can possibly be expected to include a keyboard 48 or other conventional means of data entry.

Finally, a display 50 allows the practitioner to present the various options available to him to define the various pacing configurations. The display can take the form shown in FIG. 4, with a schematic representation of the different regions of the heart identifying the key targets:

For the right atrium RA: atrial appendage AA, lateral wall LW and atrial septum AS;

For the right ventricle RV: output flow track region OFT, low septum LS, medium and high septum, MS and HS, and bottom APEX;

For the coronary system CS (by which the left ventricle is stimulated): great cardiac vein GCV, lateral vein LV, posterolateral vein PLV, posterior vein PV and middle cardiac vein MCV.

Figure 5:
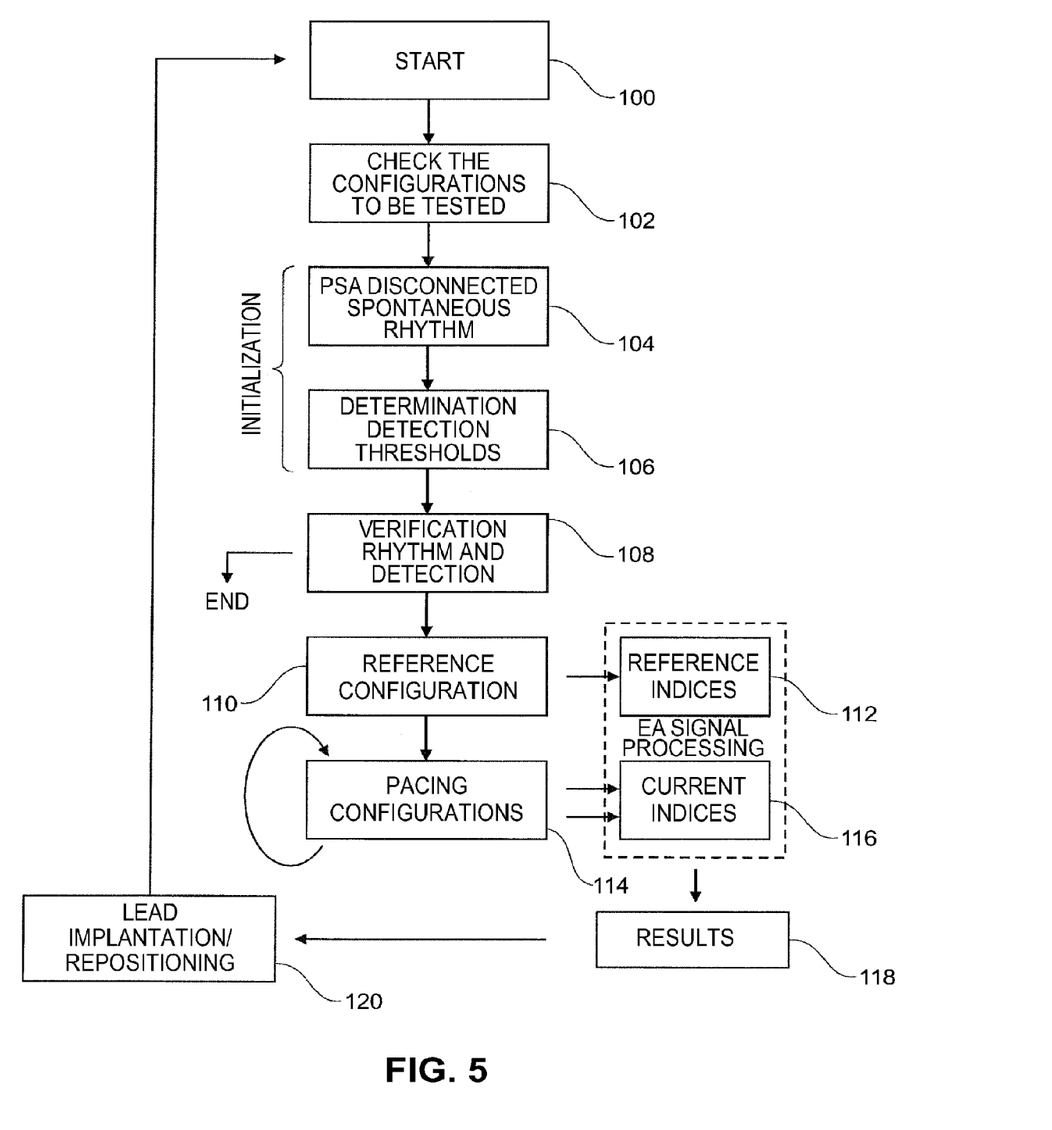
FIG. 5 is a flow chart describing the various stages of a preferred method of implementing the elements of the present invention.

FIG. 5 shows an example of a preferred method in accordance with the present invention for the selection of the best pacing configuration at the time of implantation. After the various initializations (step 100), the practitioner checks the configurations to be tested (step 102). The reference condition which is then used for the various comparisons can be that corresponding to the particular patient's spontaneous rhythm in order to allow the spontaneous rhythm be expressed (step 104). For safety, the external stimulator (PSA) is normally disconnected from the lead; it is connected only for the later steps of testing the various pacing configurations.

The detection thresholds for synchronization of the sensor signals are also determined during this initial phase (step 106).

The external generator (PSA) is then connected, stimulation is applied and various checks are performed, including the stability of the rhythm (step 108).

An initial configuration is then tested (step 110), the EA signal processing producing (block 112) the sought composite indexes Ind1, Ind2, Ind3 and/or Ind4 (it should be understood however, that obtaining two of these indexes is usually sufficient).

Other pacing configurations are then tested with different electrode switching (step 114). Note that the setting of the AVD and VVD is generally not changed at this step (rather they are changed at a later step of possible optimization after site selection and monitoring of the patient). It may in particular be programmed with a short AVD selected in the range from 80 to 100 ms, and a VVD equal to zero.

The corresponding indexes are evaluated (block 116) and compared with the reference indexes, to give an overall result (step 118).

The practitioner can then change the location of the leads or reposition them (block 120) and repeat the process described above (back to step 100), to again give new results in step 118.

The successive results obtained are compared in order to determine the pacing configuration providing the optimal efficiency. For example, the practitioner can test various configurations. The first set of test configurations is a "standard" set including:

Spontaneous rhythm (as reference);

Stimulation of the right ventricle RV alone (for purposes of diagnosis or as a reference configuration);

Stimulation of the left ventricle only;

Conventional bi-ventricular pacing (which can also be chosen as the reference configuration), with concomitant stimulation of both right and left ventricles RV-LV.

The diagnosis is used to evaluate the sensitivity of the indexes in the worst conditions of stimulation, for a patient with heart failure; it is not, however, to consider such stimulation as a possible programmable pacing configuration.

Then, all possible configurations involving repositioning the lead or the addition of an additional lead V+ are tested. The repositioning of the RV and LV leads involves repeating the test for basic configurations RV only, LV only, and RV-LV. Adding an additional lead V+ to stimulate the left or right ventricle involves testing all possible pacing combinations:

Bi-ventricular (concomitant stimulation LV–V+ or RV–V+),

Tri-ventricular pacing (concomitant stimulation V+, RV and LV),

Multi-ventricular pacing (concomitant stimulation on several electrodes of a multielectrode lead, and on RV and LV).

The configuration in spontaneous rhythm is always reassessed at the beginning of each series of tests, and indexes are compared with those obtained the first time (reference configuration). If a substantial variation of the index in the spontaneous condition is established, a warning is displayed, and the practitioner should check the patient's condition: indeed, a change in the index should not normally occur, otherwise it is a symptom of deterioration of the patient, to be taken into account immediately.

The practitioner can for example test the following three sets of configurations shown in the following table:

| Configurations | Implanted lead | Brought changes | Configurations to be tested (new or modified) |
|---|---|---|---|
| n°1 | RA, RV, LV | — | Spontaneous, LV only, BiV |
| n°2 | RA, RV, LV | RV repositioning | Spontaneous, BiV |
| n°3 | RA, RV, V+, LV | V+ added | Spontaneous, BiV+, TriV |

Of all the tested configurations, the one that is selected is the one that produces the optimal of the composite index(es) (the minimum value with the indexes Ind1 to Ind4 exemplified above).

Later, after the stimulation pacing sites have been selected, a comparable analysis algorithm can be implemented to test configurations differing in the settings of the AVD and/or the VVD to maximize the values of these parameters. It may be the same after implantation in the patient follow-up, in order to assess the impact of a change in the pacing configuration and/or in the setting of the AVD and VVD.

It is thus possible to calculate the indexes for each pair of values {AVD, VVD}, then to choose the pair that is associated with the highest index value. The analysis can be done by trying to optimize the composite indexes Ind1, Ind2, Ind3 and/or Ind4 described above (the optimization typically is on two of these indexes).

It is also possible to use the indexes to monitor the patient's pathology in the long term, in order to assess the deleterious effects of remodeling and prevent the occurrence of an adverse event resulting from the increase of the heart failure status. It is then to assess the evolution over time of a given index to detect a deterioration in the patient's condition and send a warning to the practitioner, for example, to change the therapy (optimized pacing configuration, change in the settings of AVD and VVD, medication, etc.).

Figure 6:
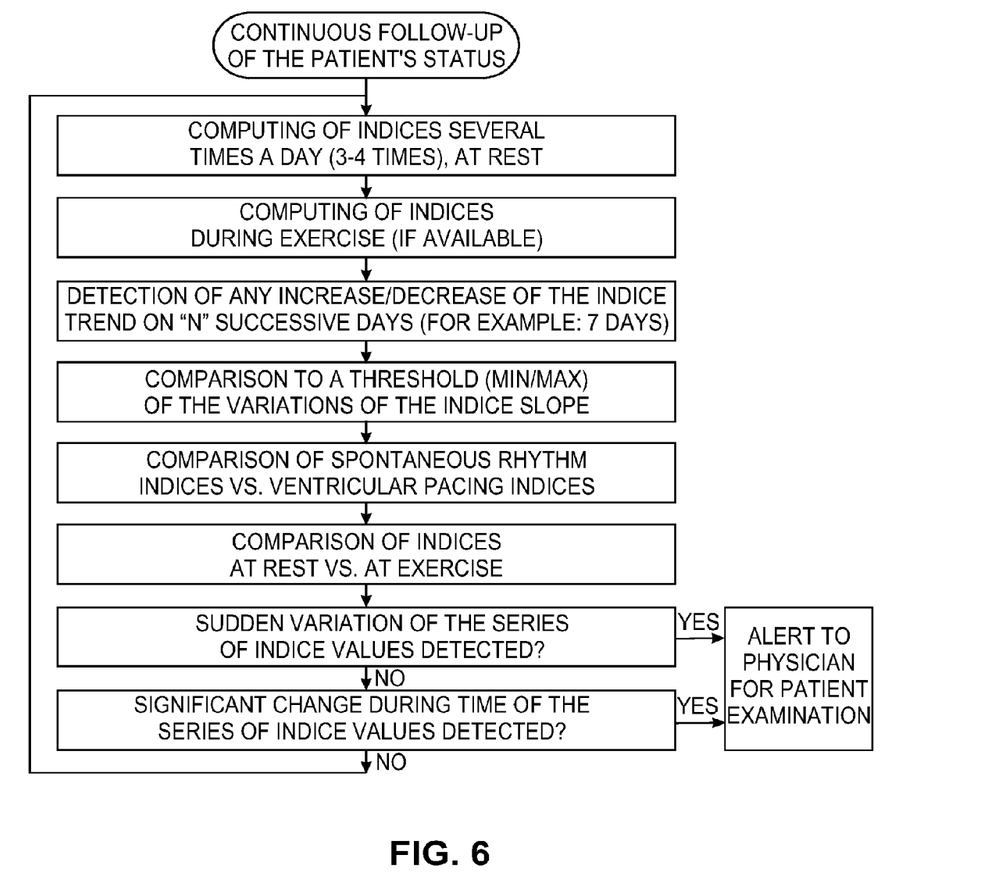
FIG. 6 is a flow chart describing the various stages of the long-term patient's monitoring by analysis of the evolution of one or more of the indexes calculated according to a preferred embodiment of the present invention.

FIG. 6 outlines the various steps of such a patient follow-up on the long-term by analysis of the evolution of one or more of the indexes Ind1, Ind2, Ind3 and/or Ind4 described above. For example, for a continuous follow-up of the patient's status, the first step involves computing of indexes several times a day (3-4 times), while the patient is at rest. Next, computing of the same indexes occurs during exercise (if available). This is followed by detection of any increase/decrease of the index trend on "N" successive days (for example: N=7 days), followed by a comparison (i) to a threshold (min/max) of the variations of the index slope, (ii) of spontaneous rhythm indexes vs. ventricular pacing indexes, and (iii) of indexes at rest vs. at exercise. A test is then performed as to whether a sudden variation of the series of index values is detected. If yes, then an alert is given to the physician for patient examination; and if no then a test is performed as to whether there is significant change during time of the series of index values detected. If the result of the latter test is yes, then an alert is sent to physician for patient examination; and otherwise the routine returns to the initial step of computing of indexes several times a day (3-4 times), while the patient is at rest).

One skilled in the art will understand the present invention is not limited by, and may be practice by other than the foregoing embodiments described, which are presented for purposes of illustration and not of limitation.

What is claimed is:

1. An implantable medical device comprising:
   a sensor configured to generate an endocardial acceleration (EA) signal representative of activity of a patient's heart;
   one or more circuits configured to:
      identify within the EA signal at least one EA signal component corresponding to at least one peak of endocardial acceleration;
      extract from the at least one EA signal component at least two characteristic parameters, the at least two characteristic parameters relating to at least two different types of characteristics of the at least one EA signal component;
      generate a composite index based on a combination of the at least two characteristic parameters;
      determine a plurality of values of the composite index for a plurality of pacing configurations; and
      select a current pacing configuration from among the plurality of pacing configurations based on the plurality of values of the composite index.

2. The device of claim 1, wherein the one or more circuits are configured to identify within the EA signal a first EA signal component corresponding to a first peak of endocardial acceleration and a second EA signal component corresponding to a second peak of endocardial acceleration.

3. The device of claim 2, wherein the one or more circuits are configured to isolate and process in the EA signal the first EA signal component and the second EA signal component during one cardiac cycle between two successive ventricular events, wherein the first EA signal component corresponds to the first peak of endocardial acceleration associated with an isovolumetric ventricular contraction, and wherein the second EA signal component corresponds to the second peak of endocardial acceleration associated with an isovolumetric ventricular relaxation.

4. The device of claim 2, wherein the one or more circuits are further configured to deliver pacing pulses to be applied to electrodes configured to be located at at least one right ventricular pacing site and at least one left ventricular pacing site in a modifiable pacing configuration.

5. The device of claim 2, wherein the at least two different types of characteristics to which the at least two characteristic parameters relate are selected from among the following:
   a peak-to-peak amplitude (PEA1) of the first EA signal component;
   a first time interval (TstEA1) between a beginning of a cardiac cycle and a beginning of the first EA signal component;
   a second time interval (LargEA1) between the beginning of the first EA signal component and a peak associated with the first EA signal component; or
   a third time interval (Syst) representative of a duration of a systole, the third time interval between the beginning of the first EA signal component and a beginning of the second EA signal component.

6. The device of claim 5, wherein at least one of the beginning of the first EA signal component or the beginning of the second EA signal component comprises a time at which an energy envelope of the respective EA signal component exceeds a threshold value.

7. The device of claim 5, wherein the at least one electronic circuit is configured to generate the composite index based on the TstEA1.

8. The device of claim 7, wherein the at least one electronic circuit is configured to generate the composite index based on a combination of the TstEA1 and the LargEA1.

9. The device of claim 8, wherein the at least one electronic circuit is configured to generate the composite index based on a combination of the TstEA1, the LargEA1, and the Syst.

10. The device of claim 9, wherein the composite index comprises a composite index Ind1=(TstEA1×LargEA1)/(Syst×PEA1).

11. The device of claim 9, wherein the composite index comprises a composite index Ind2=(TstEA1×LargEA1)/[(Syst−LargEA1)×PEA1].

12. The device of claim 9, wherein the composite index comprises a composite index Ind3=(TstEA1×LargEA1)/(Syst).

13. The device of claim 7, wherein the composite index comprises a composite index Ind4=(TstEA1)/(PEA1).

14. The device of claim 1, wherein the at least one electronic circuit is configured to select the current pacing configuration associated with a lowest value or a highest value of the plurality of values of the composite index.

15. The device of claim 1, further comprising:
an atrial lead carrying the sensor;
a right ventricular lead carrying a first distal electrode configured to be placed in one or more positions within a right ventricle in the plurality of pacing configurations; and
a left ventricular lead carrying a second distal electrode configured to be placed in one or more positions within a left ventricle in the plurality of pacing configurations.

16. The device of claim 1, wherein the one or more circuits are configured to transmit data relating to one or more of the plurality of values of the composite index to an external programming device configured to assess an effectiveness of one or more of the plurality of pacing configurations based on the one or more of the plurality of values of the composite index.

17. A method comprising:
generating, using an acceleration sensor of an implantable medical device, an endocardial acceleration (EA) signal representative of activity of a patient's heart;
identifying within the EA signal a first EA signal component corresponding to a first peak of endocardial acceleration and a second EA signal component corresponding to a second peak of endocardial acceleration;
extracting from at least one of the first EA signal component and the second EA signal component at least two characteristic parameters, the at least two characteristic parameters relating to at least two different types of characteristics of the at least one of the first EA signal component and the second EA signal component;
generating a composite index based on a combination of the at least two characteristic parameters;
determining a plurality of values of the composite index for a plurality of pacing configurations; and
selecting a current pacing configuration for the implantable medical device from among the plurality of pacing configurations based on the plurality of values of the composite index.

18. The method of claim 17, wherein identifying the first EA signal component and the second EA signal component comprises isolating and processing in the EA signal the first EA signal component and the second EA signal component during one cardiac cycle between two successive ventricular events, wherein the first EA signal component corresponds to the first peak of endocardial acceleration associated with an isovolumetric ventricular contraction, and wherein the second EA signal component corresponds to the second peak of endocardial acceleration associated with an isovolumetric ventricular relaxation.

19. The method of claim 17, wherein the at least two different types of characteristics to which the at least two characteristic parameters relate are selected from among the following:
a peak-to-peak amplitude (PEA1) of the first EA signal component;
a first time interval (TstEA1) between a beginning of a cardiac cycle and a beginning of the first EA signal component;
a second time interval (LargEA1) between the beginning of the first EA signal component and a peak associated with the first EA signal component; or
a third time interval (Syst) representative of a duration of a systole, the third time interval between the beginning of the first EA signal component and a beginning of the second EA signal component.

20. The method of claim 19, wherein the at least one electronic circuit is configured to generate the composite index based on the TstEA1.

21. The method of claim 20, wherein the at least one electronic circuit is configured to generate the composite index based on a combination of the TstEA1 and the LargEA1.

22. The method of claim 21, wherein the at least one electronic circuit is configured to generate the composite index based on a combination of the TstEA1, the LargEA1, and the Syst.

23. The method of claim 22, wherein the composite index comprises one of the following composite indexes:

$$Ind1 = (TstEA1 \times LargEA1)/(Syst \times PEA1);$$

$$Ind2 = (TstEA1 \times LargEA1)/[(Syst - LargEA1) \times PEA1];$$
or $$Ind3 = (TstEA1 \times LargEA1)/(Syst).$$

24. The method of claim 20, wherein the composite index comprises a composite index Ind4=(TstEA1)/(PEA1).

25. The method of claim 17, wherein the selected current pacing configuration is associated with a lowest value or a highest value of the plurality of values of the composite index.

* * * * *